(12) United States Patent
Hyodo et al.

(10) Patent No.: US 10,213,094 B2
(45) Date of Patent: Feb. 26, 2019

(54) SLACK CORRECTION MECHANISM, MANIPULATOR, AND MANIPULATOR SYSTEM

(71) Applicant: OLYMPUS CORPORATION, Tokyo (JP)

(72) Inventors: Ryoji Hyodo, Tokyo (JP); Kosuke Kishi, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 253 days.

(21) Appl. No.: 15/248,008

(22) Filed: Aug. 26, 2016

(65) Prior Publication Data

US 2016/0360949 A1    Dec. 15, 2016

Related U.S. Application Data

(63) Continuation of application No. PCT/JP2015/053451, filed on Feb. 9, 2015.

(30) Foreign Application Priority Data

Feb. 26, 2014    (JP) .................................. 2014-034974

(51) Int. Cl.
*A61B 1/00* (2006.01)
*A61B 1/005* (2006.01)
(Continued)

(52) U.S. Cl.
CPC ........ *A61B 1/0052* (2013.01); *A61B 1/00045* (2013.01); *A61B 1/0057* (2013.01);
(Continued)

(58) Field of Classification Search
CPC ................ A61B 1/0052; A61B 1/0057; A61B 1/00045; A61B 1/04; A61B 1/06;
(Continued)

(56) References Cited

U.S. PATENT DOCUMENTS

| 4,203,430 A | 5/1980 | Takahashi |
| 2009/0306475 A1 | 12/2009 | Yamamoto et al. |

(Continued)

FOREIGN PATENT DOCUMENTS

| CN | 102573600 A | 7/2012 |
| EP | 2448 463 | 5/2012 |

(Continued)

OTHER PUBLICATIONS

International Search Report dated Apr. 28, 2015 issued in PCT/JP2015/053451.
Extended Supplementary European Search Report dated Nov. 7, 2017 received in 15755359.5.

*Primary Examiner* — Timothy J Neal
(74) *Attorney, Agent, or Firm* — Scully, Scott, Murphy & Presser, P.C.

(57) ABSTRACT

The slack correction mechanism includes a distal-end pulley that is rotatable with respect to a given axis, a distal-end wire wound around the distal-end pulley, a first supporting part including a first base, a first friction portion around which the distal-end wire is looped on one side and a first biasing portion that biases the distal-end wire in a pulling direction on one end side with respect to the first friction portion, the first supporting part being adapted to support one side of the distal-end wire, and a second supporting part including a second base, a second friction portion around which the distal-end wire is looped on the other side and a second biasing portion that biases the distal-end wire in a pulling direction on the other side with respect to the second friction portion, the second supporting part being adapted to support the other side of the distal-end wire.

8 Claims, 16 Drawing Sheets

(51) Int. Cl.
  *B25J 9/10* (2006.01)
  *G02B 23/24* (2006.01)
  *A61B 34/00* (2016.01)
  *A61B 1/04* (2006.01)
  *A61B 1/06* (2006.01)
  *A61B 1/31* (2006.01)
  *A61B 17/00* (2006.01)

(52) U.S. Cl.
  CPC .................. *A61B 1/04* (2013.01); *A61B 1/06* (2013.01); *A61B 1/31* (2013.01); *A61B 34/70* (2016.02); *B25J 9/1045* (2013.01); *G02B 23/2476* (2013.01); *A61B 2017/00327* (2013.01); *A61B 2034/715* (2016.02)

(58) Field of Classification Search
  CPC ................ A61B 1/31; A61B 2034/715; A61B 2017/00327; A61B 34/70; B25J 9/1045
  See application file for complete search history.

(56) References Cited

U.S. PATENT DOCUMENTS

| | | |
|---|---|---|
| 2010/0331820 A1 | 12/2010 | Prisco et al. |
| 2011/0282154 A1 | 11/2011 | Umemoto |
| 2012/0289973 A1 | 11/2012 | Prisco et al. |

FOREIGN PATENT DOCUMENTS

| | | |
|---|---|---|
| JP | S48-28518 B | 9/1973 |
| JP | H11-253389 A | 9/1999 |
| JP | 2000001218 A | 1/2000 |
| JP | 2001-314410 A | 11/2001 |
| JP | 2002-200091 A | 7/2002 |
| JP | 4145464 B2 | 9/2008 |
| JP | 2012-504016 A | 2/2012 |
| JP | 2013-215505 A | 10/2013 |
| WO | 2011/108840 A2 | 9/2011 |
| WO | WO 2013/154158 A1 | 10/2013 |
| WO | 2013/180041 A1 | 12/2013 |

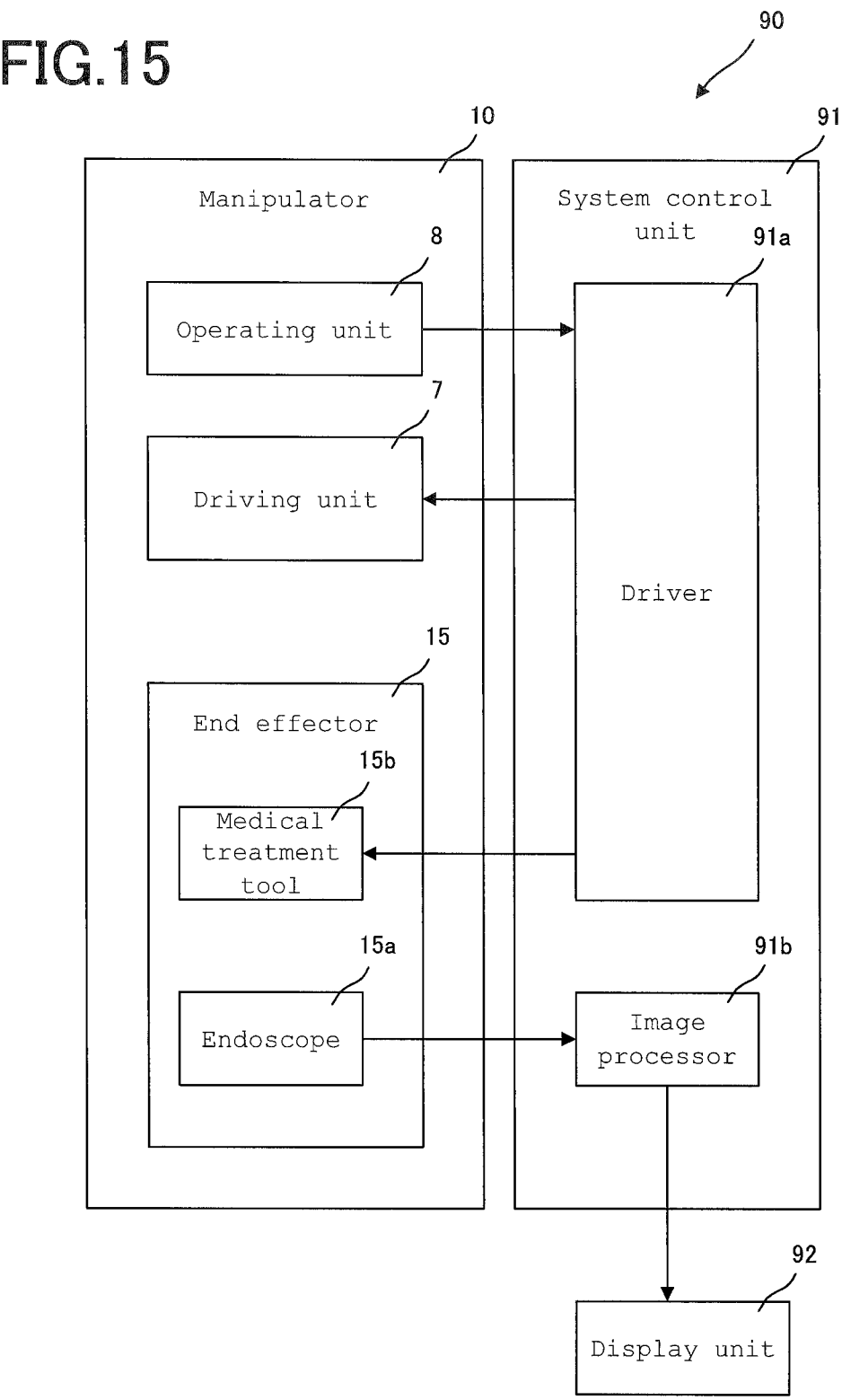

SLACK CORRECTION MECHANISM, MANIPULATOR, AND MANIPULATOR SYSTEM

CROSS-REFERENCE TO RELATED APPLICATIONS

This application is a continuation claiming priority on the basis of Japan Patent Application No. 2014-034974 applied in Japan on Feb. 26, 2014 and based on PCT/JP2015/053451 filed on Feb. 9, 2015. The contents of both the PCT application and the Japan Application are incorporated herein by reference.

BACKGROUND OF THE INVENTION AND RELATED ART STATEMENT

The present invention relates to a slack correction mechanism used with an apparatus in which a distal end member mounted on a pulley is put in operation by pulling or letting out a wire wound around the pulley for the purpose of correcting slack in the wire as well as a manipulator and a manipulator system.

FIGS. 16A, 16B and 16C is a schematic view of one example of one typical prior art manipulator.

So far there has been a manipulator used in which a wire 130 is wound on one side around a driving pulley 140 and on the other side around a driven pulley 120 for power transmission, as shown in FIG. 16A.

When the driving pulley 140 is rotated by an operator (not shown) from a neutral state of FIG. 16A in a direction indicated by an action arrow A1, the wire 130 tends to move in a direction indicated by an action arrow B in association with the rotation of the driving pulley 140 in the direction indicated by the action arrow A1. Because the necessary load is applied to the driven pulley 120 when it starts to rotate, however, the driven pulley 120 does not rotate even upon rotation of the driving pulley 140. For this reason, there is an elongation 131 of the wire 130 pulled by the driving pulley 140, and there is slack 132 in the wire 130 let out by the driving pulley 140, as shown in FIG. 16B.

When the driving pulley 140 is then reversed in a direction indicated by an action arrow A2 as shown typically in FIG. 16C, the pulling force is not transmitted to the driven pulley 120 until the dynamic slack 132 in the wire 130, shown in FIG. 16B, is removed, with the result that a distal-end member 121 attached to the driven pulley 120 is unlikely to go into operation even with the operation of the driving pulley 140, as shown in FIG. 16C.

Japanese Patent No. 4145464 discloses the technology of pulling the slack in the wire by means of a spring for removal of such slack 132 as shown in FIG. 16B thereby reducing operational delay shown in FIG. 16C.

SUMMARY OF INVENTION

According to one embodiment, a slack correction mechanism includes
a distal-end pulley that is rotatable with respect to a given axis,
a wire wound around the distal-end pulley,
a first supporting part including a first base, a first friction portion which extends out from the first base and around which the wire wound around the distal-end pulley is looped on one side and a first biasing portion that biases the wire in a pulling direction on one end side with respect to the first friction portion, the first supporting part being adapted to support one side of the wire, and
a second supporting part including a second base, a second friction portion which extends out from the second base and around which the wire wound around the distal-end pulley is looped on the other side and a second biasing portion that biases the wire in a pulling direction on the other side with respect to the second friction portion, the second supporting part being adapted to support the other side of the wire.

According to one embodiment, a manipulator includes
a distal-end part that takes rotatable hold of the distal-end pulley by pulling or letting out the distal-end wire, and
the slack correction mechanism.

According to one embodiment, a manipulator system includes
the manipulator,
a control unit for controlling the manipulator, and
a display unit for displaying an image acquired through the manipulator, wherein:
the manipulator includes an endoscope having a viewing optical system, an imaging device and a lighting optical system, and
the control unit permits an image acquired through the endoscope to be displayed on the display unit.

BRIEF DESCRIPTION OF DRAWINGS

FIG. 15 is a block diagram for one example of the manipulator system according to one embodiment.

DESCRIPTION OF EMBODIMENTS

Some embodiments are now explained.

Figure 1:
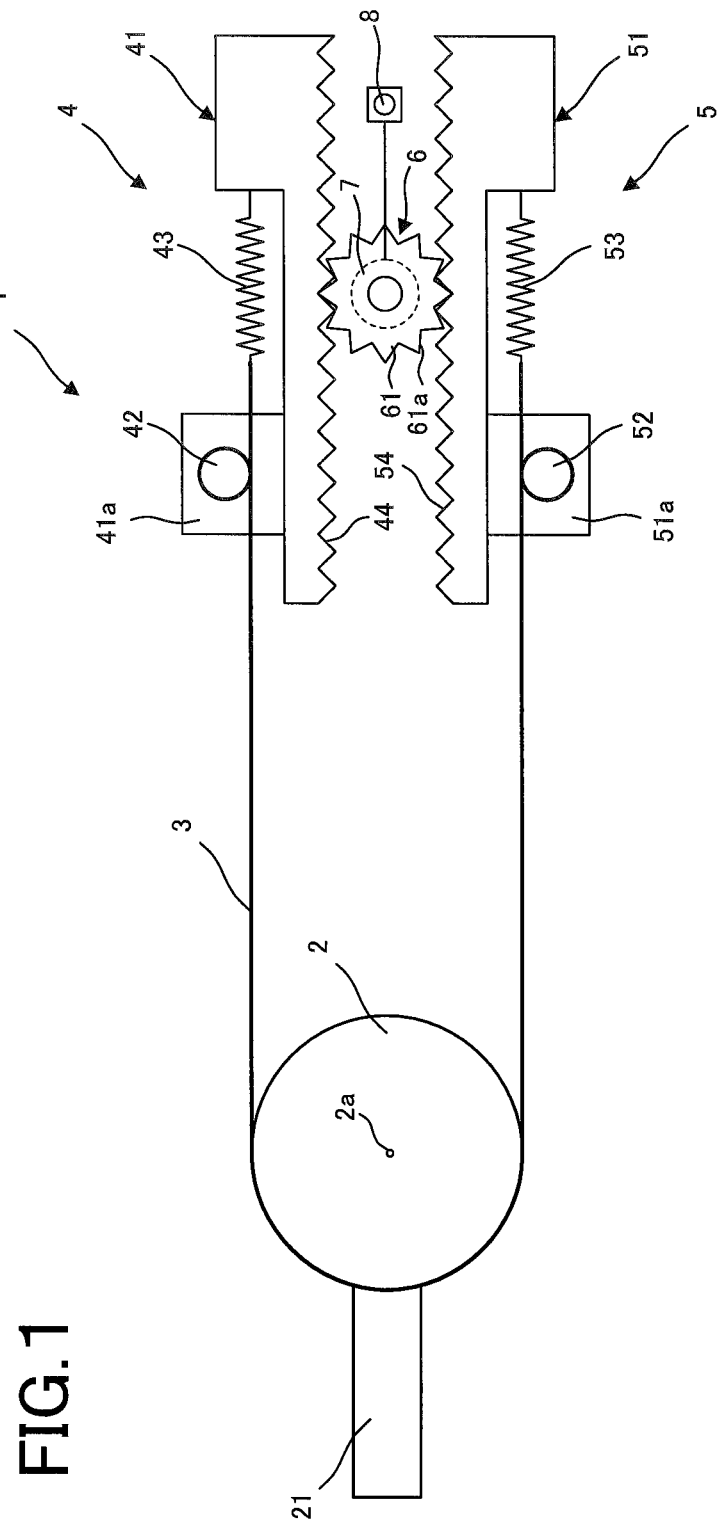
FIG. 1 is a schematic view of one example of the slack correction mechanism 1 according to the first embodiment.

FIG. 1 is a schematic view of one example of the slack correction mechanism 1 according to the first embodiment.

The slack correction mechanism 1 according to the first embodiment includes a distal-end pulley 2 that is rotatable with respect to a given axis 2a, a distal-end wire 3 wound around the distal-end pulley 2, a first supporting part 4 including a first base 41, a first friction portion 42 which extends out from the first base 41 and around which the distal-end wire 3 wound around the distal-end pulley 2 is looped on one side and a first coil spring 43 defining a first biasing portion which biases the distal-end wire 3 in a pulling direction on one end side with respect to the first friction portion 42, the first supporting part 4 being adapted to support one side of the distal-end wire 3, and a second supporting part 5 including a second base 51, a second friction portion 52 which extends out from the second base 51 and around which the wire 3 wound around the distal-end pulley 2 is looped on the other side and a second coil spring 53 that biases the distal-end wire 3 in a pulling direction on the other side with respect to the second friction portion 52, the second supporting part 5 being adapted to support the other side of the distal-end wire 3.

It is here to be noted that the first coil spring 43 defines the first biasing portion and the second coil spring 53 defines the second biasing portion. The coil springs are not necessarily used for the first and the second biasing portion; they may be each formed of any member capable of biasing the distal-end wire 3. The first 43 and the second coil spring 53 should preferably have the same biasing force.

The distal-end pulley 2 is rotatably attached to the given axis 2a, and has the distal-end wire 3 wound along its outer circumference. As an example, the distal-end pulley 2 is preferably provided with a distal-end member 21 that rotates with the distal-end pulley 2. For instance, the distal-end member 21 may be an electrode or the like of a high-frequency treatment tool.

The distal-end wire 3 wound around the distal-end pulley 2 is supported on one side to the first supporting part 4 and on the other side to the second supporting part 5.

The first supporting part 4 includes the first base 41, the first friction portion 42 and the first coil spring 43. The first base 41 supports one side of the distal-end wire 3, and is movable in a pulling or delivery direction of the distal-end wire 3. Extending from a first step 41a of the first base 41 toward the distal-end wire 3, the first friction portion 42 is formed into a columnar configuration, and one side of the distal-end wire 3 wound around the distal-end pulley 2 is looped around the first friction portion 42. The first coil spring 43 biases the distal-end wire 3 in the pulling direction on one end side of the distal-end wire 3 with respect to the first friction portion 42.

The second supporting part 5 includes the second base 51, the second friction portion 52 and the second coil spring 53. The second base 51 supports one side of the distal-end wire 3, and is movable in a pulling or delivery direction of the distal-end wire 3. Extending out from a second step 51a of the second base 51 toward the distal-end wire 3, the second friction portion 52 is formed into a columnar configuration, and one side of the distal-end wire 3 wound around the distal-end pulley 2 is looped around the second friction portion 52. The second coil spring 53 biases the distal-end wire 3 in the pulling direction on one end side of the distal-end wire 3 with respect to the second friction portion 52.

In the slack correction mechanism 1 according to the first embodiment, one end of the distal-end wire 3 is fixed to one end of the first coil spring 43, the other end of the distal-end wire 3 is fixed to the first base 41 of the first supporting part 4, the other end of the distal-end wire 3 is fixed to one end of the second coil spring 53, and the other end of the second coil spring 53 is fixed to the second base 51 of the second supporting part 5. In other words, one end of the distal-end wire 3 is supported to the first supporting part 4 indirectly by way of the first coil spring 43, and the other end of the distal-end wire 3 is supported to the second supporting part 5 indirectly by way of the second coil spring 53.

Preferably, the slack correction mechanism 1 according to the first embodiment includes an interlocking part 6 activated such that when one of the first supporting part 4 and the second supporting part 5 moves in the pulling direction of the distal-end wire 3, the other moves in the delivery direction of the distal-end wire 3. Provision of the interlocking part 6 makes sure interlocking movement of the first supporting part 4 and the second supporting part 5 for unerring operation.

In the slack correction mechanism 1 according to the first embodiment, the interlocking part 6 is made up of a pinion 61 having mating teeth 61a on its circumference. The first supporting part 4 includes a first rack 44 in mesh with the mating teeth 61a of the pinion 61, and the second supporting part 5 includes a second rack 54 in mesh with the mating teeth 61a of the pinion 61. In the slack correction mechanism 1 according to the first embodiment, the mating position where the mating teeth 61a are in mesh with the first rack 44 is opposed to the mating position where the mating teeth 61a are in mesh with the second rack 54 with respect to the center of rotation of the pinion 61.

As the pinion 61 rotates, therefore, it causes the first supporting part 4 including the first rack 44 in mesh with the mating teeth 61a and the second supporting part 5 including the second rack 54 to move in opposite directions.

The slack correction mechanism 1 according to the first embodiment may include a driving unit 7 for driving the interlocking part 6, and an operating unit 8 that is put by an operator in operation to drive the driving unit 7. The driving unit 7 here may be an electrically-operated member such as a motor, and the operating unit 8 here may be a joystick, a pointing device or a liquid crystal pad. Provision of the driving unit 7 and operating unit 8 makes sure smooth and unerring operation. Note here that the interlocking part 6 may be manually rotated by the operating unit 8 such as a handle without recourse to the driving unit 7.

The operation of the slack correction mechanism 1 according to the first embodiment is now explained.

Figure 2:
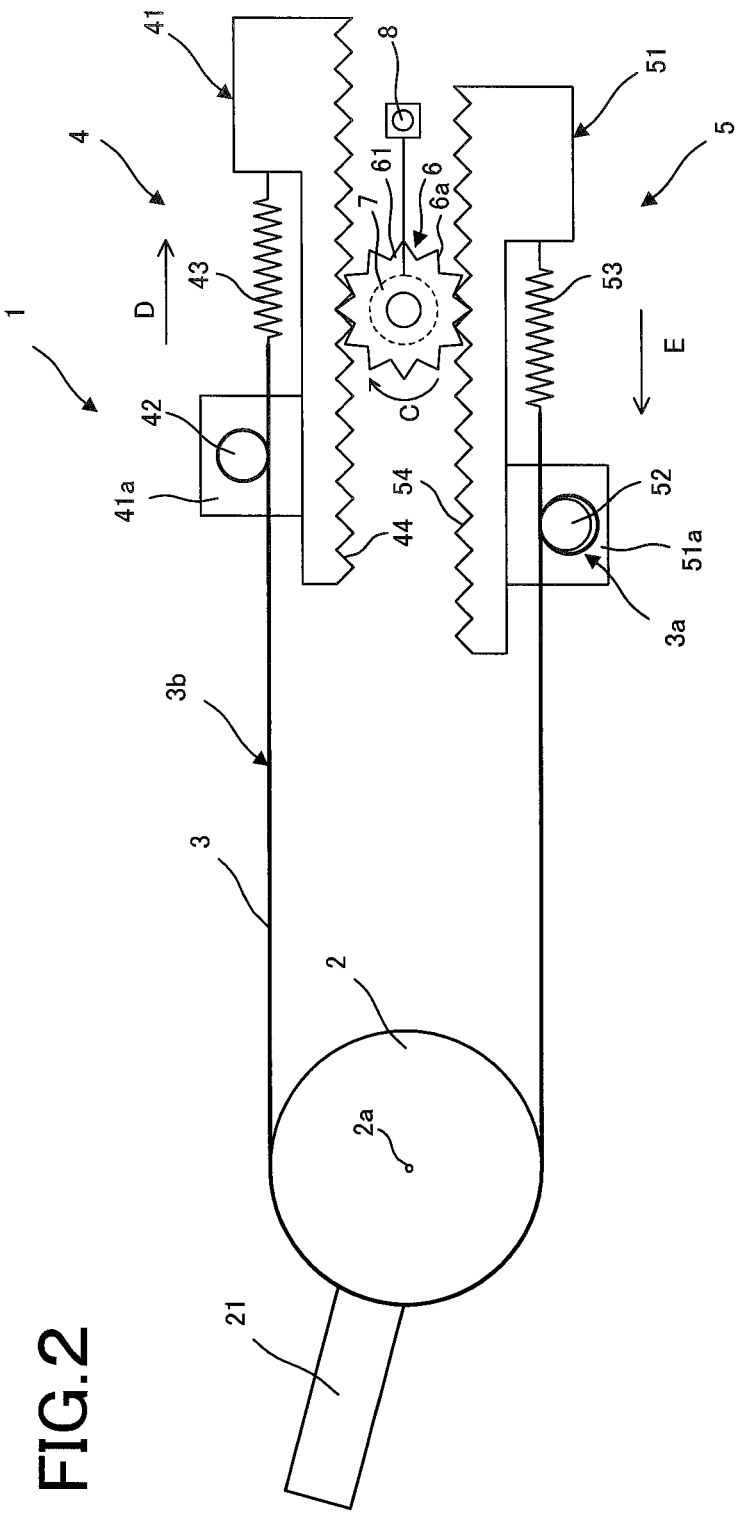
FIG. 2 is a schematic view of one operating state of the slack correction mechanism 1 according to the first embodiment.
Figure 3:
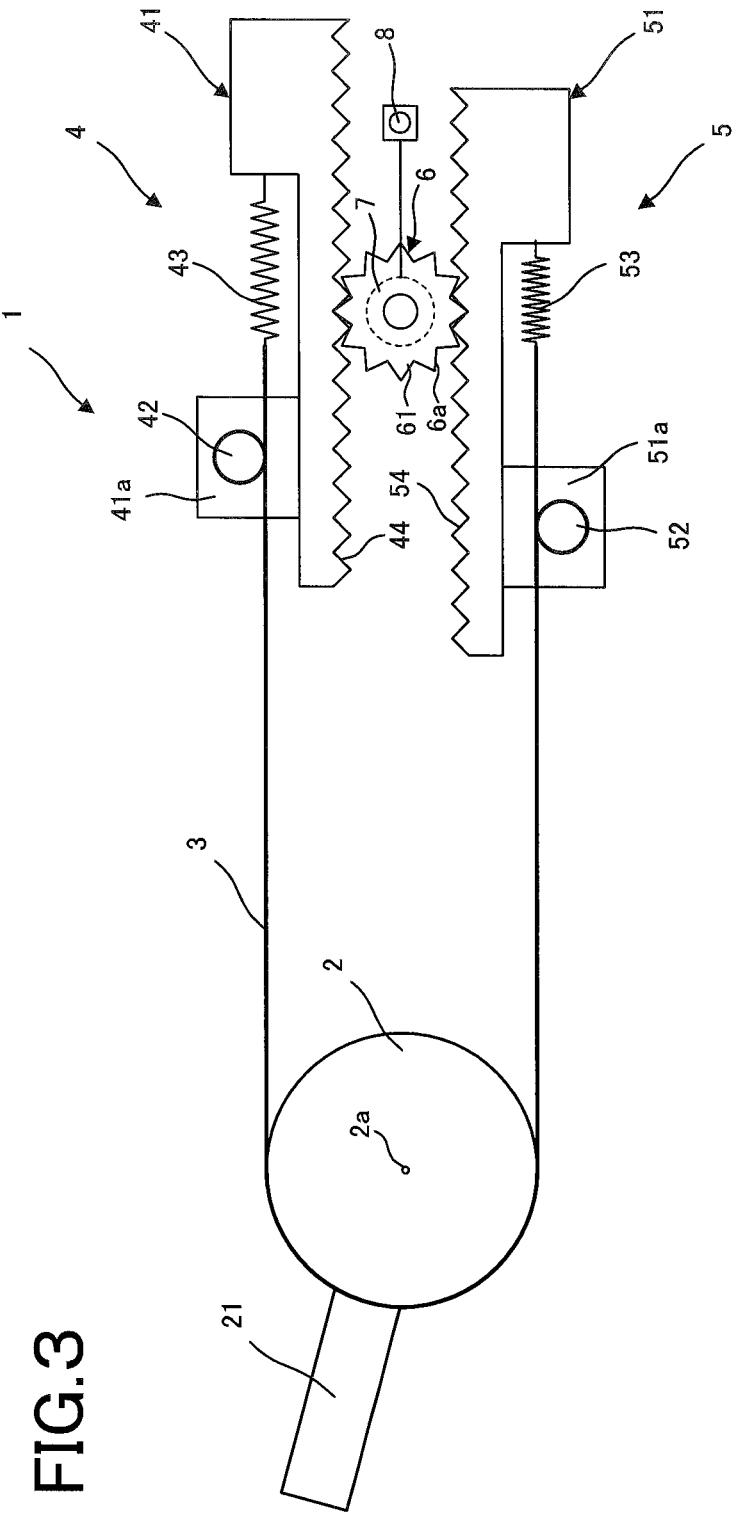
FIG. 3 is a schematic view of one operating state of the slack correction mechanism 1 according to the first embodiment.
Figure 4:
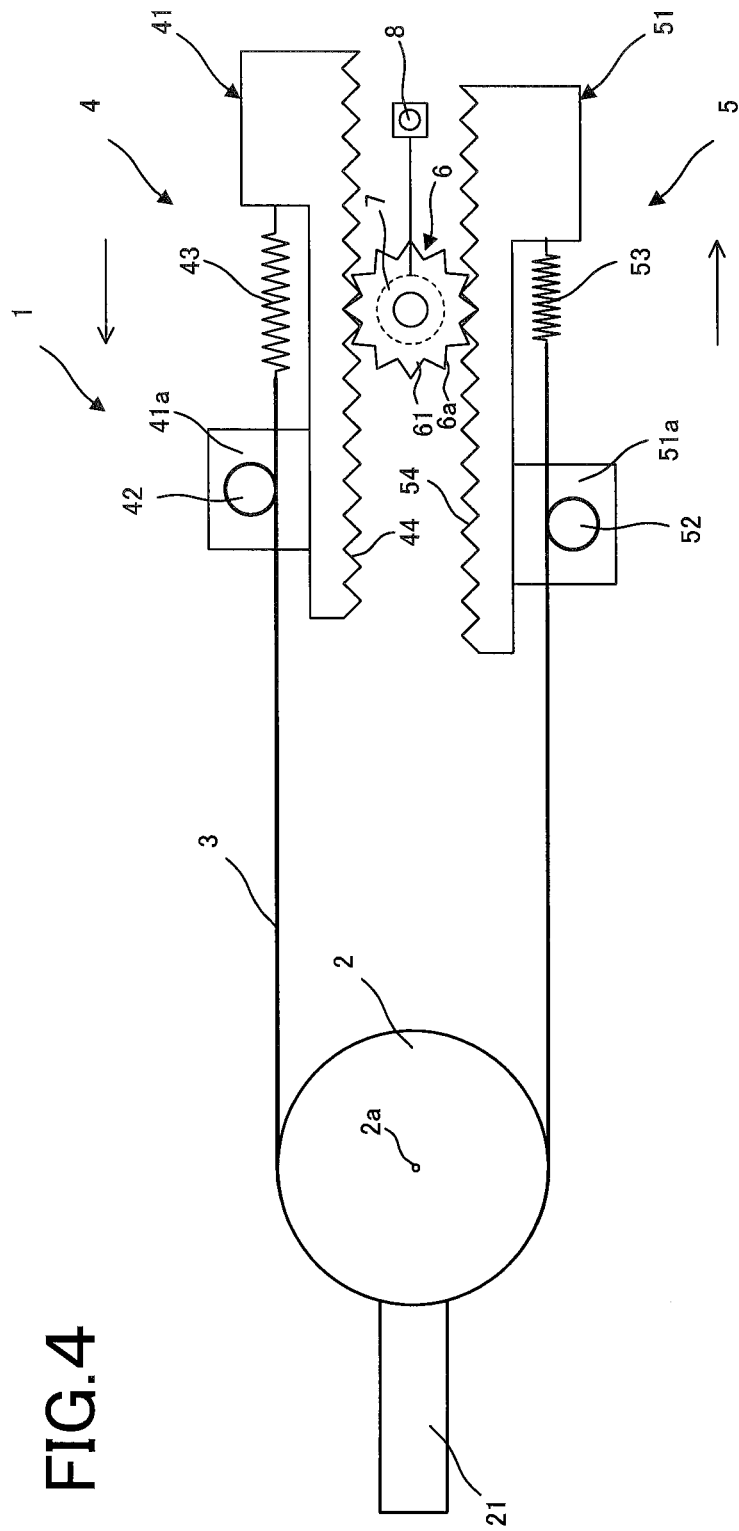
FIG. 4 is a schematic view of one operating state of the slack correction mechanism 1 according to the first embodiment.

FIGS. 2, 3 and 4 are schematic views of operating states of the slack correction mechanism 1 according to the first embodiment.

In the slack correction mechanism 1 according to the first embodiment, as the pinion 61 of the interlocking part 6 is rotated in a direction indicated by an action arrow C in FIG. 2, it causes the first supporting part 4 to move in a direction indicated by an action arrow D and the second supporting part 5 to move in a direction indicated by an action arrow E. At this time, there is a slack 3a in the other side of the distal-end wire 3 looped around the second friction portion 52 of the second supporting part 5, and there is an invisible elongation 3*b* of one side of the distal-end wire 3. However, these remain fixed by friction between the second friction portion 52 and the distal-end wire 3.

As shown in FIG. 3, this slack 3*a* is overcome as the distal-end wire 3 is pulled by the biasing force of the second coil spring 53. As the wire 3 is then driven in the opposite direction as shown in FIG. 4, it starts to go into operation even when there is no movement by that slack amount. Typically, the distal-end member 21 does not usually start to move unless the first 4 and the second supporting part 5 are positioned symmetrically with respect to the pinion 61, but in the slack correction mechanism 1 according to the first embodiment, the distal-end member 21 starts to go rapidly into operation before the first supporting part 4 and the second supporting part 5 are positioned symmetrically with respect to the pinion 61.

With the slack correction mechanism 1 according to the first embodiment, the slack in the distal-end wire 3 is corrected by the first coil spring 43 and the second coil spring 53. It is thus possible to reduce the operational delay of the distal-end member 21 for unerring operation. Further, because the distal-end wire 3 is not looped in its entirety, an assembling steps count diminishes, resulting in improved assembling capability and ease of initial tension adjustment as well. Furthermore, there is no need for using a caulking member or the like for connection of the distal-end wire 3, possibly ending up with smooth operation.

The second embodiment is now explained.

Figure 5:
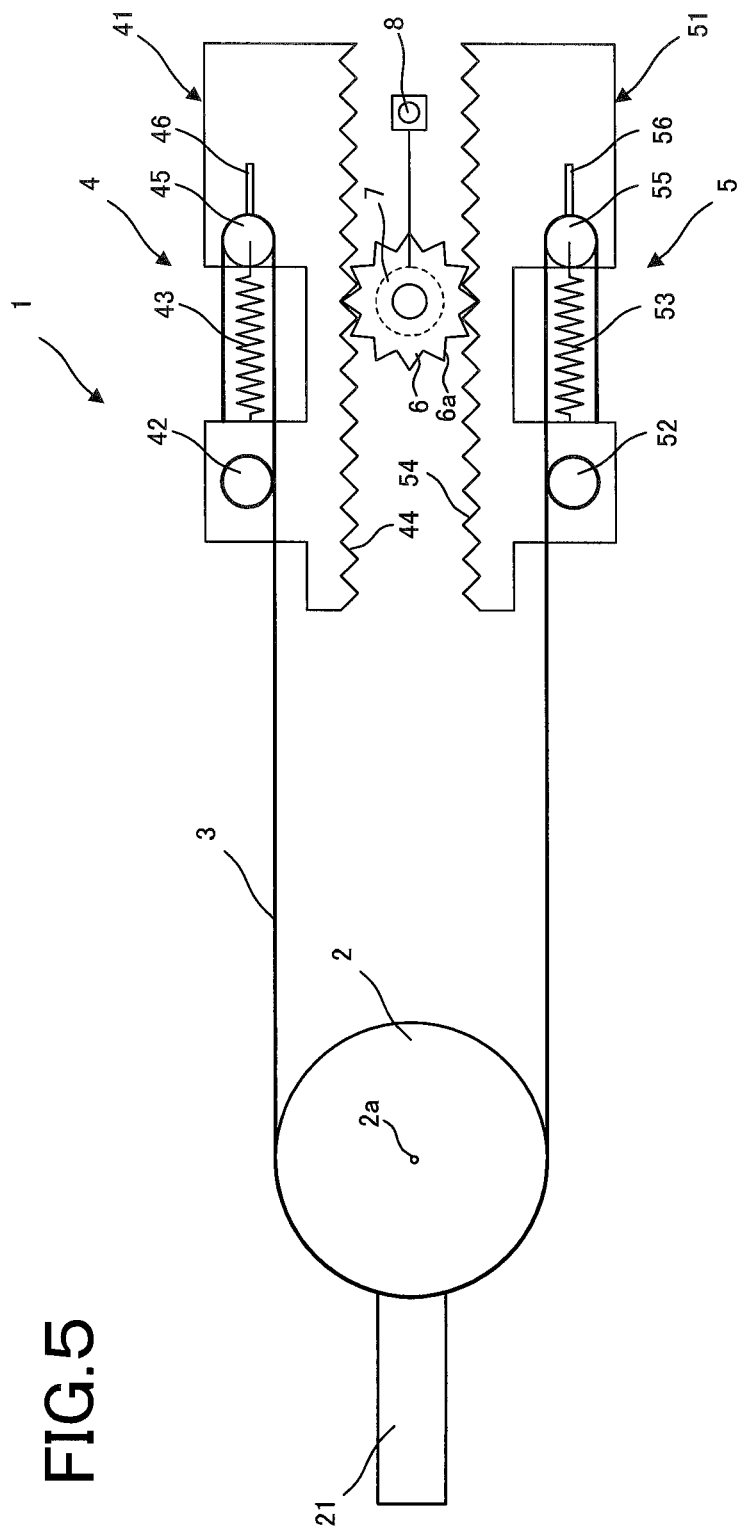
FIG. 5 is a schematic view of one example of the slack correction mechanism 1 according to the second embodiment.

FIG. 5 is a schematic view of one example of the slack correction mechanism 1 according to the second embodiment.

The slack correction mechanism 1 according to the second embodiment is similar in structure to that of the first embodiment with the exception that the first supporting part 4 and the second supporting part 5 are structurally different from those in the first embodiment. Accordingly, only the structures of the first supporting part 4 and the second supporting part 5 are now explained.

In the slack correction mechanism 1 according to the second embodiment, the first base 41 includes a first tension pulley 45 that supports one end of the first coil spring 43 and is movable in the pulling direction of the distal-end wire 3, and the second base 51 includes a second tension pulley 55 that supports one end of the second coil spring 53 and is movable in the pulling direction of the distal-end wire 3. The distal-end wire 3 is wound around the first tension pulley 45 on one end side with respect to the first friction portion 42, fixed at one end to the first base 41, wound around the second tension pulley 55 on the other end side with respect to the second friction portion 55, and fixed at the other end to the second base 51.

To put it another way, in order from one end to the other end, the distal-end wire 3 is supported to the first base 41, wound around the first tension pulley 45, looped around the first friction portion 42, wound around the distal-end pulley 2, looped around the second friction portion 52, wound around the second tension pulley 55, and supported to the second base 51.

The first base 41 is provided with a guide 46 for the first tension pulley, and the first tension pulley 45 is movably supported to that guide 46. The distal-end wire 3 may be wound around the first tension pulley 45 in such a way as to form a part of a spiral. In other words, the position where the distal-end wire 3 is supported to the first base 41 may be spaced away from the surface where the distal-end wire 3 is looped around the first friction portion 42.

The second base 51 is provided with a guide 56 for the second tension pulley, and the second tension pulley 55 is movably supported to that guide 56. The distal-end wire 3 may be wound around the second tension pulley 55 in such a way as to form a part of a spiral. In other words, the position where the distal-end wire 3 is supported to the second base 51 may be spaced away from the surface where the distal-end wire 3 is looped around the second friction portion 52.

The operation of the slack correction mechanism 1 according to the second embodiment is now explained.

Figure 6:
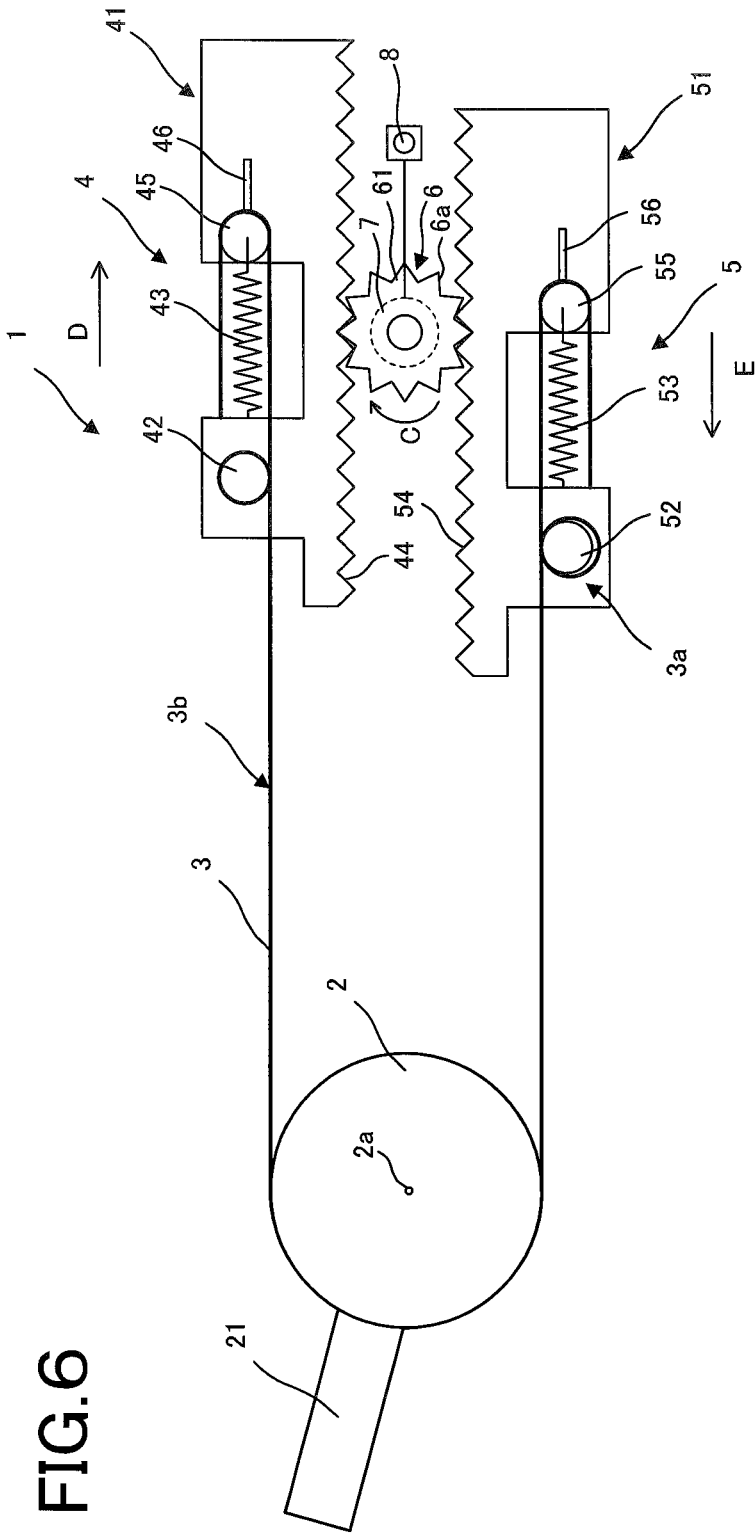
FIG. 6 is a schematic view of one operating state of the slack correction mechanism 1 according to the second embodiment.
Figure 7:
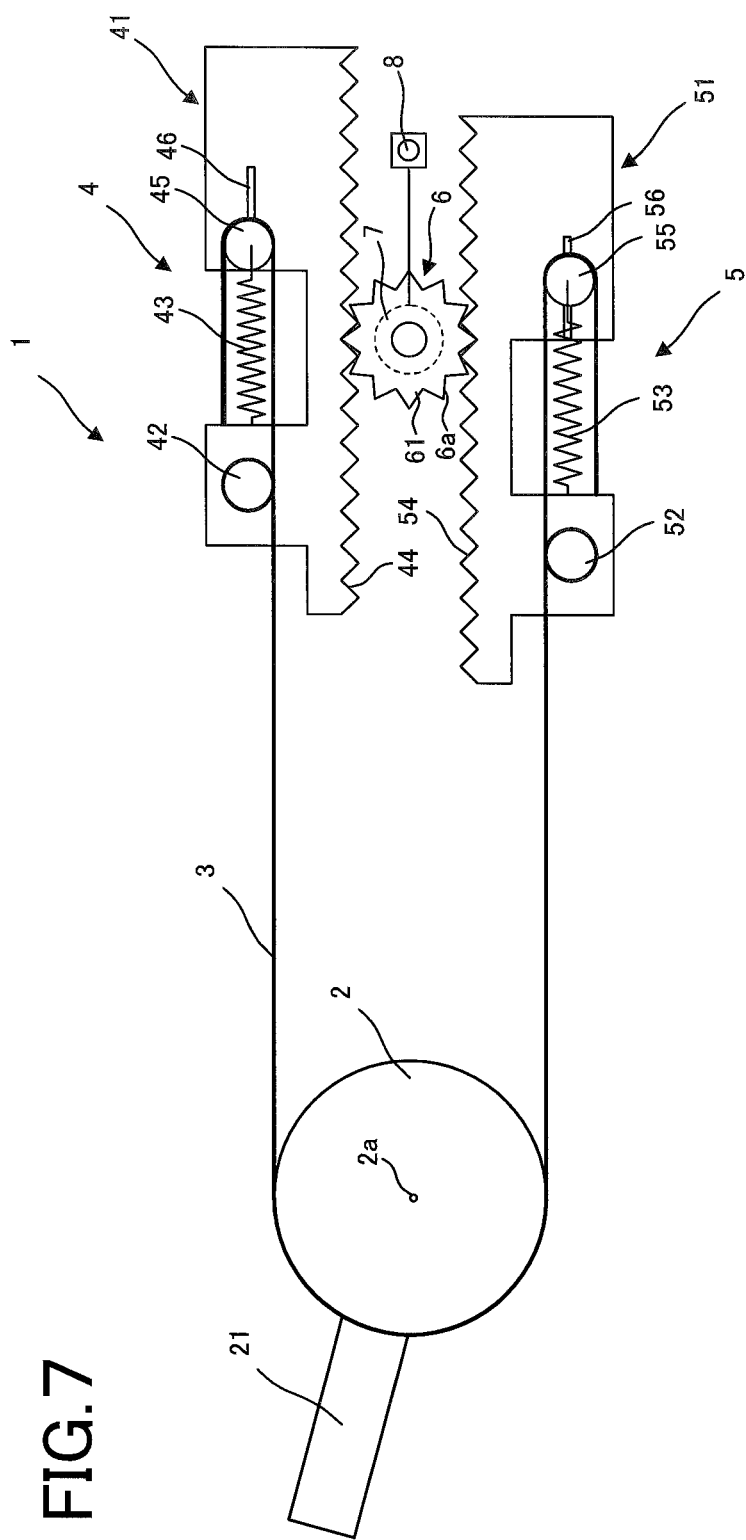
FIG. 7 is a schematic view of one operating state of the slack correction mechanism 1 according to the second embodiment.
Figure 8:
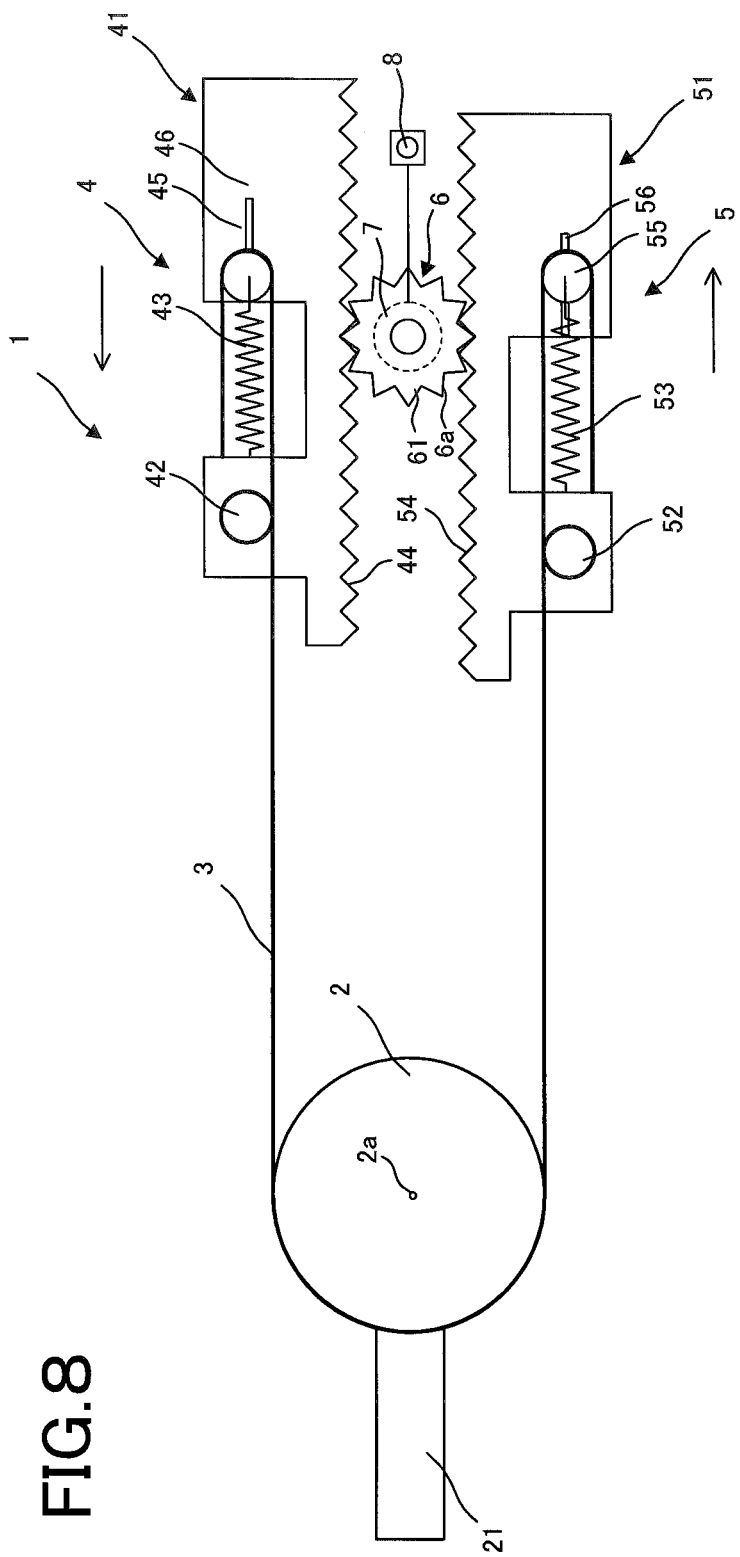
FIG. 8 is a schematic view of one operating state of the slack correction mechanism 1 according to the second embodiment.

FIGS. 6, 7 and 8 are schematic views of operating states of the slack correction mechanism 1 according to the second embodiment.

In the slack correction mechanism 1 according to the second embodiment, as the pinion 61 of the interlocking part 6 is rotated in the direction indicated by an action arrow C in FIG. 6, it causes the first supporting part 4 to move in the direction indicated by an action arrow D and the second supporting part 5 to move in the direction indicated by an arrow action E. At this time, there is a slack 3*a* in the other side of the distal-end wire 3 looped around the second friction portion 52 of the second supporting part 5, and there is an invisible elongation 3*b* on one side of the distal-end wire 3. However, these remain fixed by friction between the second friction portion 52 and the distal-end wire 3.

Such slack 3*a* is overcome as the second tension pulley 55 moves the guide 56 for the second tension pulley under the biasing force of the second coil spring 53 to pull the distal-end wire 3 wound around the second tension pulley 55. As the wire 3 is then driven in the opposite direction as shown in FIG. 8, it starts to go into operation even when there is no movement by that slack amount. Typically, the distal-end member 21 does not usually start to move unless the first supporting part 4 and the second supporting part 5 are positioned symmetrically with respect to the pinion 61, but in the slack correction mechanism 1 according to the first embodiment, the distal-end member 21 starts to go rapidly into operation before the first supporting part 4 and the second supporting part 5 are positioned symmetrically with respect to the pinion 61.

As described above, the slack correction mechanism 1 according to the second embodiment has, in addition to the advantage of the first embodiment, an advantage of reducing the elongation of the springs to half, because the distal-end wire 3 is looped around the first friction portion 42 and the second friction portion 52, resulting in improved assembling capability, ease of length adjustment for the distal-end wire 3 and facility in initial tension adjustment. Further, the slack correction mechanism 1 according to the second embodiment makes use of the rack-and-pinion mechanism, contributing more to simple arrangement and unerring operation.

The third embodiment is now explained.

Figure 9:
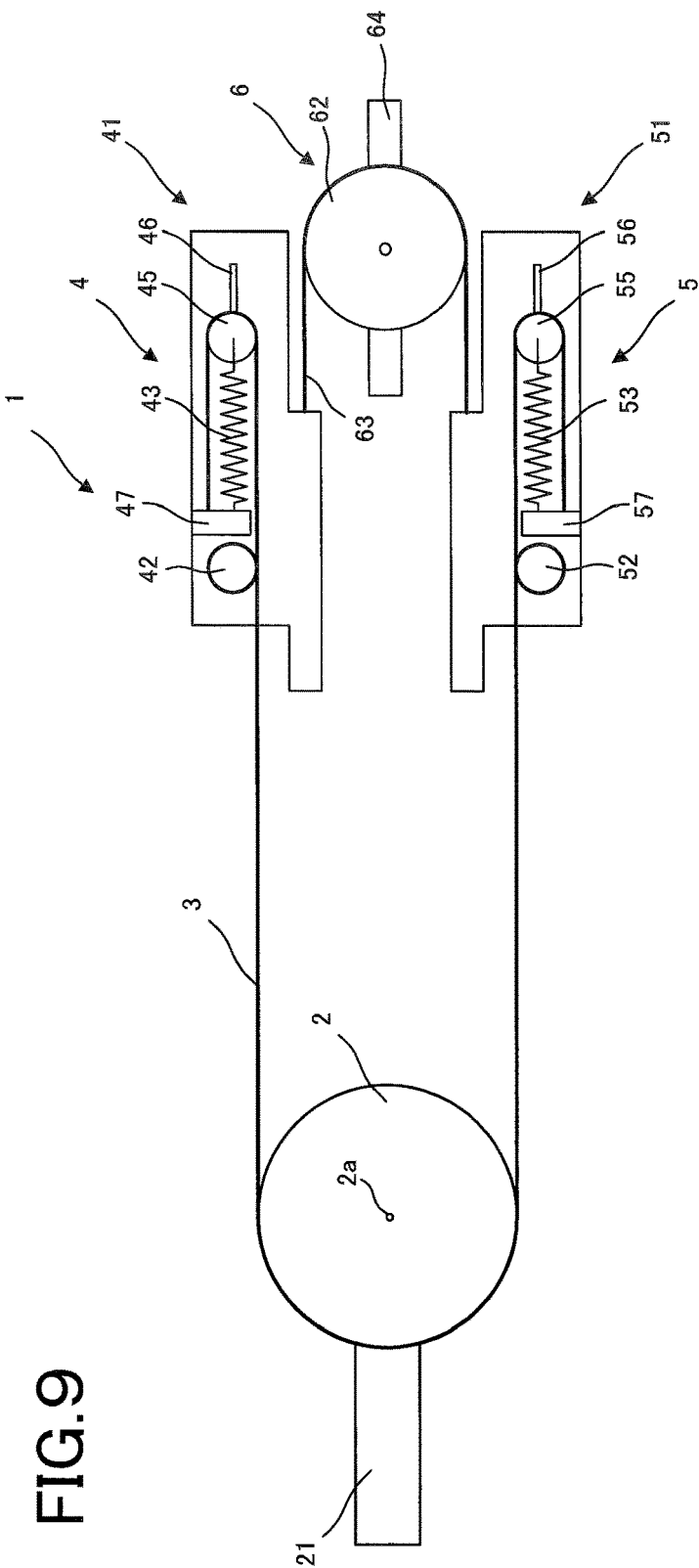
FIG. 9 is a schematic view of one example of the slack correction mechanism 1 according to the third embodiment.

FIG. 9 is a schematic view of one example of the slack correction mechanism 1 according to the third embodiment.

The slack correction mechanism 1 according to the third embodiment is similar in structure to that according to the second embodiment with the exception that the first supporting part 4 and second supporting part 5 and the interlocking part 6 are structurally different from those according to the second embodiment. Therefore, the structures of the first supporting part 4 and the second supporting part 5 and the structure of the interlocking part 6 are here explained.

In the slack correction mechanism 1 according to the third embodiment, the first supporting part 4 is provided with a first wall 47 that extends out in the same direction as the direction of extending the first friction portion 42 out from the first base 41, and one end of the distal-end wire 3 and one end of the first coil spring 43 are supported to the first wall 47. Likewise, the second supporting part 5 is provided with a second wall 57 that extends out in the same direction as the direction of extending the second friction portion 52 out from the second base 51, and one end of the distal-end wire 3 and one end of the second coil spring 53 are supported to the second wall 57.

It is here to be noted that instead of using the first wall 47 and the second wall 57 for the first supporting part 4 and the second supporting part 5 in the third embodiment, the positions of the distal-end wire 3 supported to the first base 41 and the second base 51 may be spaced away from the surfaces where the distal-end wire 3 is looped around the first friction portion 42 and the second friction portion 52, as explained with reference to the second embodiment, and that the first wall 47 and the second wall 57 may be applied to the first supporting part 4 and the second supporting part 5 in the second embodiment as well.

In the slack correction mechanism 1 according to the third embodiment, the interlocking part 6 includes an interlocking pulley 62, an interlocking wire 63 and an interlocking pulley guide 64. The interlocking pulley 62 is movable with respect to the interlocking pulley guide 64. The interlocking wire 63 is supported at one end to the first base 41 and at the other end to the second base 51, and wound around the interlocking pulley 62.

With the interlocking part 6, therefore, the interlocking pulley 62 is first moved by the interlocking pulley guide 64 for initial tension setting for the distal-end wire 3 and interlocking wire 63. Then, as the interlocking part 6 is actuated to rotate the interlocking pulley 62, it causes one of the first supporting part 4 and the second supporting part 5 to be pulled and the other to be let out.

The operation of the slack correction mechanism 1 according to the third embodiment is now explained.

Figure 10:
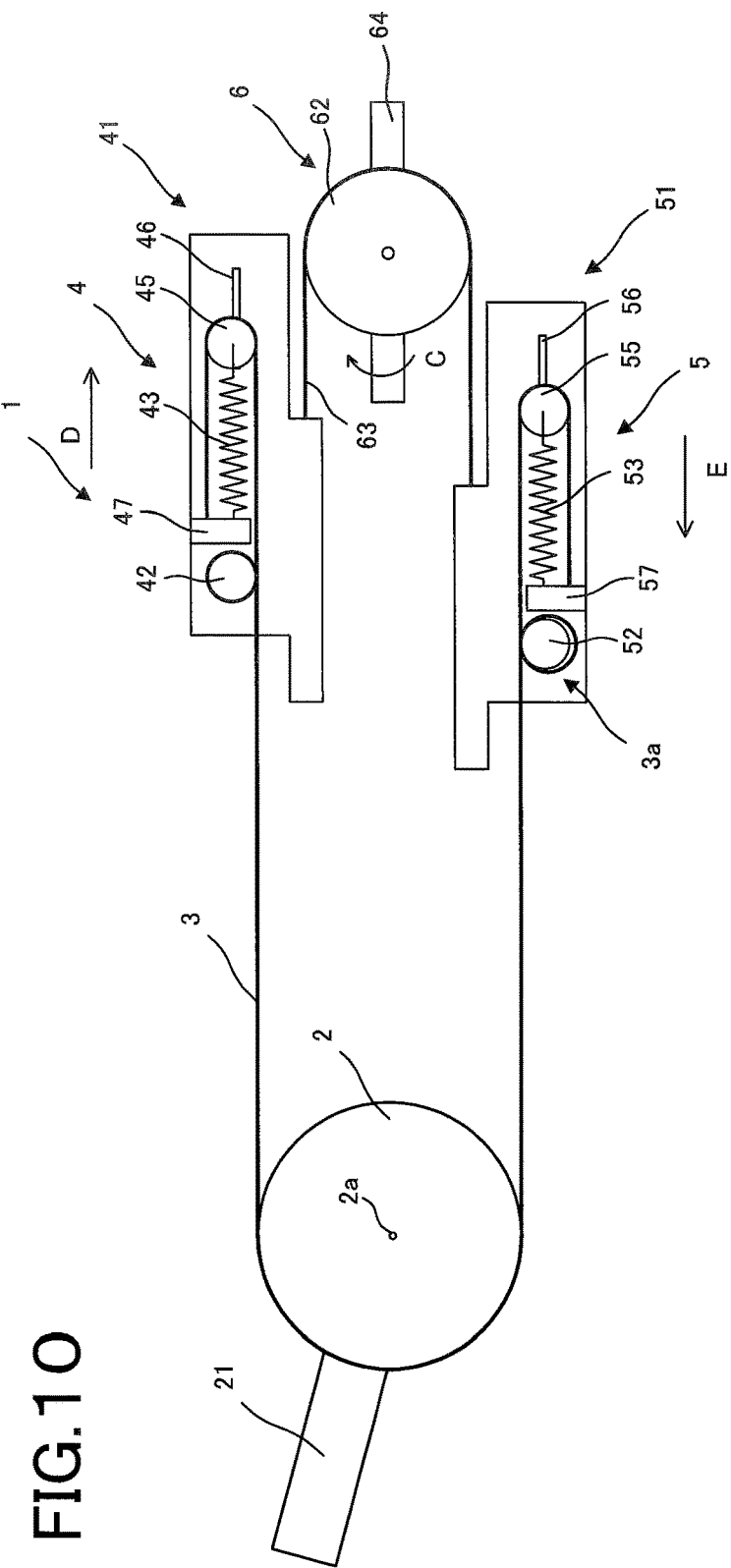
FIG. 10 is a schematic view of one operating state of the slack correction mechanism 1 according to the third embodiment.
Figure 11:
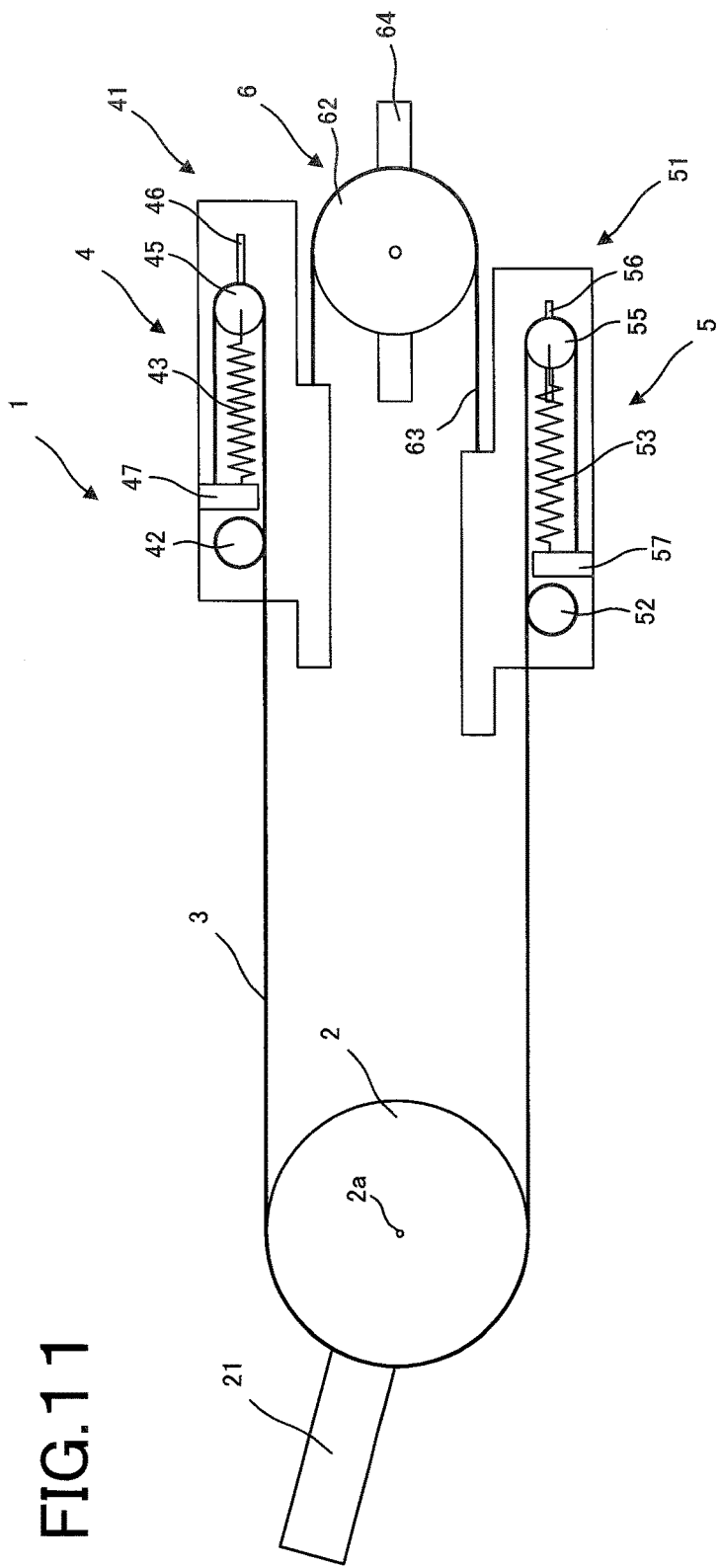
FIG. 11 is a schematic view of one operating state of the slack correction mechanism 1 according to the third embodiment.
Figure 12:
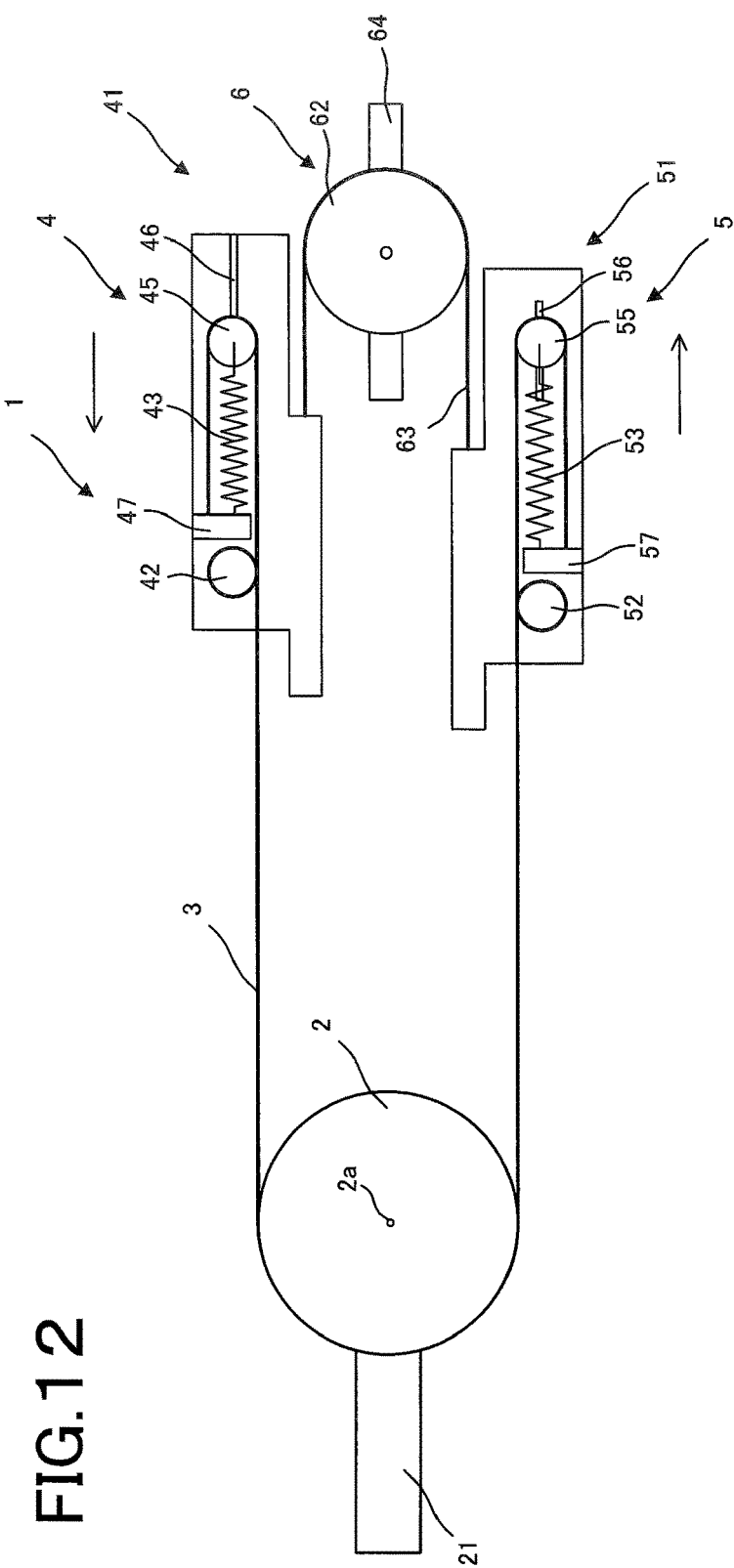
FIG. 12 is a schematic view of one operating state of the slack correction mechanism 1 according to the third embodiment.

FIGS. 10, 11 and 12 are schematic views of operating states of the slack correction mechanism 1 according to the third embodiment.

Referring to the slack correction mechanism 1 according to the third embodiment, as the interlocking part 6 goes into operation as shown in FIG. 10, it causes the interlocking pulley 62 to rotate in the direction indicated by an action arrow C and the first supporting part 4 to be pulled by the interlocking wire 63. The first supporting part 4 moves in the direction indicated by an action arrow D, and the second supporting part 5 moves in the direction indicated by an action arrow E. At this time, there is a slack 3*a* in the other side of the distal-end wire 3 looped around the second friction portion 52 of the second supporting part 5, and there is an invisible elongation 3*b* of one side of the distal-end wire 3. However, these remain fixed by friction between the second friction portion 52 and the distal-end wire 3.

Such slack 3*a* is overcome as the second tension pulley 55 moves the second tension pulley guide 56 under the biasing force of the second coil spring 53 to pull the distal-end wire 3 wound around the second tension pulley 55, as shown in FIG. 11. As the wire 3 is then driven in the opposite direction as shown in FIG. 12, it starts to go into operation even when there is no movement by that slack amount. Typically, the distal-end member 21 does not usually start to move unless the first supporting part 4 and the second supporting part 5 are positioned symmetrically with respect to the pinion 61, but in the slack correction mechanism 1 according to the third embodiment, the distal-end member 21 starts to go rapidly into operation before the first supporting part 4 and the second supporting part 5 are positioned symmetrically with respect to the interlocking pulley 62.

As described above, the slack correction mechanism 1 according to the third embodiment has, in addition to the advantage of the first embodiment, an advantage of temporarily stopping the distal-end wire 3 upon assembling, because the distal-end wire 3 is looped around the first friction portion 42 and the second friction portion 52, resulting in further improved assembling capability, more facile length adjustment for the distal-end wire 3 and more facile initial tension adjustment. Further, the initial tension setting for the distal-end wire 3 and interlocking wire 63 may be made by movement of the interlocking pulley 62 by means of the interlocking pulley guide 64, leading to more unerring initial tension adjustment.

The manipulator 10 incorporating the slack correction mechanism 1 according to one embodiment is now explained.

Figure 13:
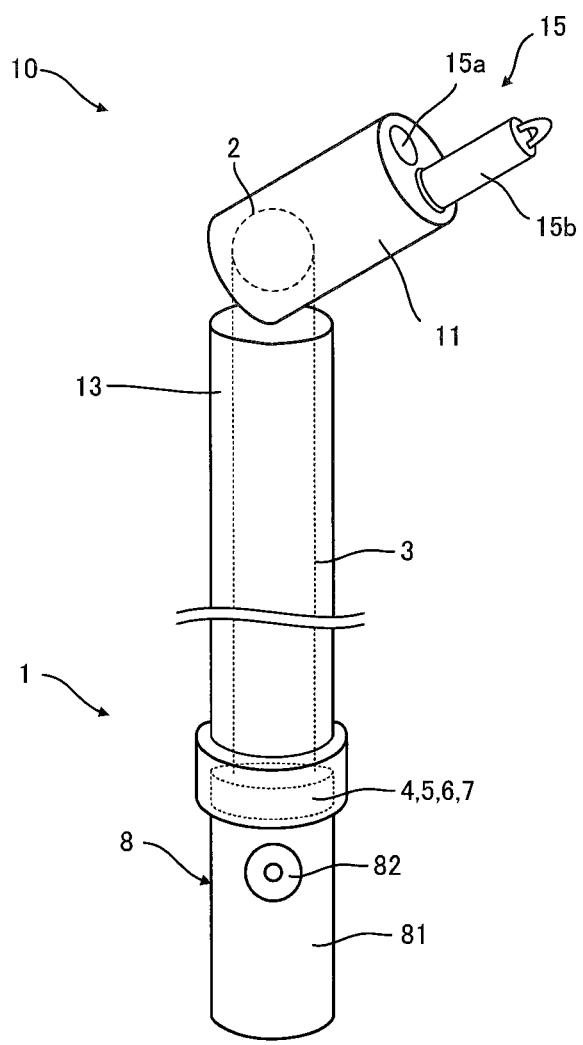
FIG. 13 is a schematic view of the manipulator according to one embodiment.

FIG. 13 is illustrative of one example of the manipulator 10 according to the embodiment described herein.

As shown in FIG. 13, the manipulator 10 according to the embodiment described herein includes a distal-end part 11, a cylindrical or tubular portion 13, and a slack correction mechanism 1.

Having a built-in distal-end pulley 2, the distal-end part 11 is opposite to a subject of interest. As shown in FIG. 13, the distal-end part 11 may have an endoscope 15*a* and a medical treatment tool 15*b* inside such as an end effector 15. Note here that the endoscope 15*a* includes a viewing optical system for viewing a subject of interest, an imaging device for taking an image of the subject of interest passing through the viewing optical system, a lighting device for lighting the subject of interest, etc.

The tubular portion 13 is provided to connect an operating unit 8 side to a distal-end part 11 side, and formed of a flexible or hard tubular member. The tubular portion 13 houses a distal-end wire 3 inside for protective purposes.

The operating unit 8 includes a grip 81, a joystick 82, and so on. While the grip 81 according to the embodiment here is shown in a rod-like member form, it is to be understood that it may take a multi-joint arm form, or a form suitable for operation of the medical treatment tool 15*b* such as a scissors' handle. The joystick 82 is provided for operation of the orientation of the distal-end part 11. Note here that the operating unit 8 may have in it the first supporting part 4 and the second supporting part 5, the interlocking part 6 and the driving unit 7 forming part of the slack correction mechanism 1.

With the manipulator 10 having such structure as described above, as the operating unit 8 is put by an operator in operation, it causes one side of the distal-end wire 3 wound around the pulley 2 to be hauled, and the distal-end part 11 to be bent in the hauling direction of the distal-end wire 3 with respect to the tubular portion 13, thus enabling the distal-end part 11 to be directed toward the subject of interest.

As described above, the manipulator 10 according to the embodiment here includes the distal-end part 11 that takes rotatable hold of the distal-end pulley 21 by pulling or letting out the distal-end wire 3, and the slack correction mechanism 1. It is thus possible for the operator to put the manipulator in unerring operation.

The surgical system 90 is now explained as an example of the manipulator system to which the manipulator 1 according to the embodiment described herein is applied.

Figure 14:
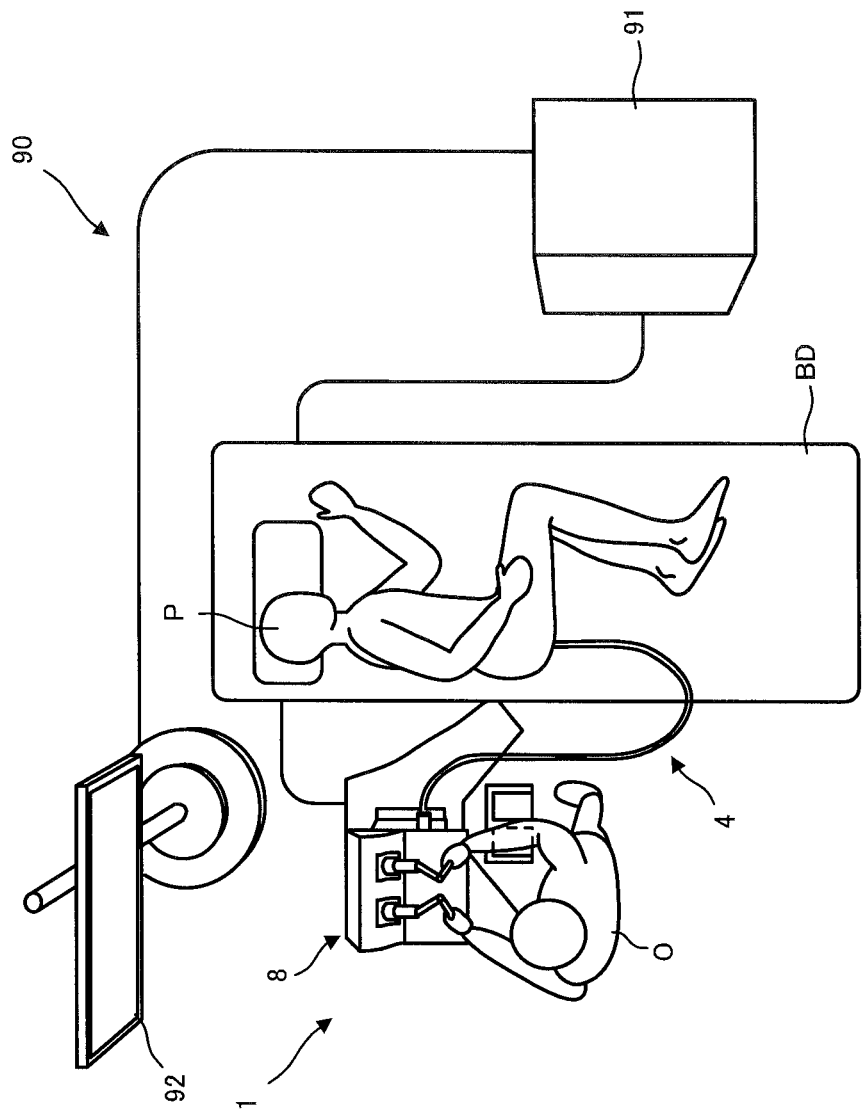
FIG. 14 is a schematic view of the manipulator system according to one embodiment.
Figure 16A:
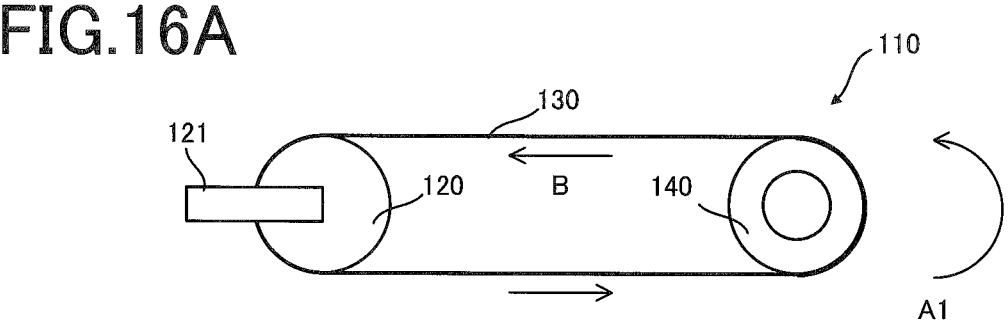
FIGS. 16A, 16B and 16C is schematically illustrative in operation of a prior art manipulator.
Figure 16B:
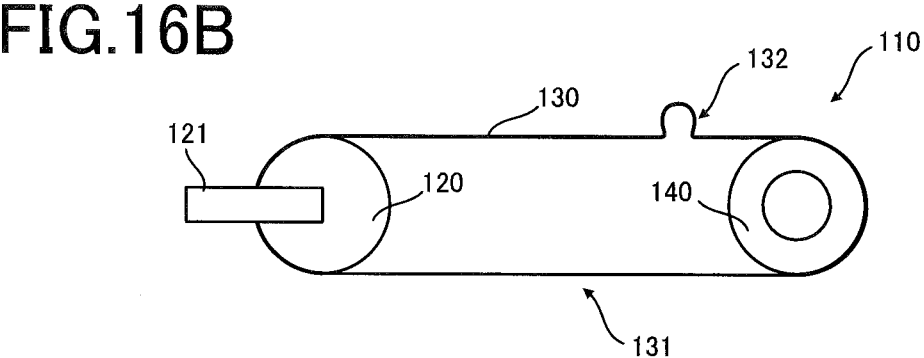
Figure 16C:
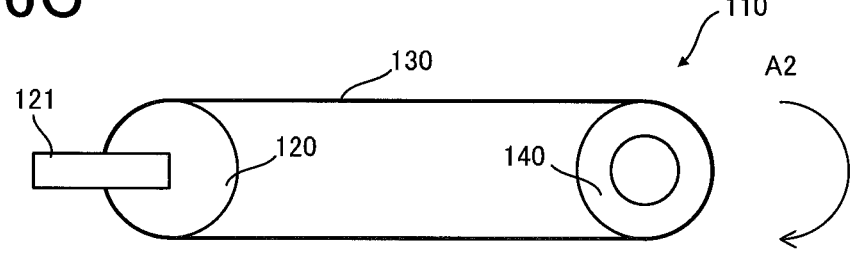

FIG. 14 is illustrative of the surgical system 90 to which the manipulator 1 according to the embodiment described herein is applied, and FIG. 15 is illustrative in system architecture of the surgical system 90 to which the manipulator 1 according to the embodiment described herein is applied.

The manipulator 1 shown in FIG. 14 is applied to the surgical system 90 according to the embodiment described herein. The surgical system 90 includes a manipulator 1 including an operating unit 8 operated by an operator O, a distal-end part 11 shown in FIG. 13, which includes a distal-end endoscope or other medical treatment tool 15b that is capable of insertion through a soft organ such as the large intestine of a patient P lying down on an operating table BD, and a tubular portion 13 that transmits an input from the operating unit 8 to the distal-end part 11 and is capable of being partially inserted into the organ, a control unit 91 for controlling the manipulator 1, and a display unit 92 for displaying an image acquired through the manipulator 1.

As shown in FIG. 14, the operating unit 8 includes a pair of operating handles mounted on an operating base, a footswitch mounted on the floor surface, etc. The operating unit 8 may have a multi-joint structure. The angle of the operating unit 8 in operation is acquired from an angle acquisition component such as an encoder and, in response to the resultant signal, the control unit 91 then puts the medical treatment tool 15b mounted on the distal end of the distal-end part 11 into operation by way of a driver 91a, as shown in FIG. 15.

An image acquired through the endoscope 15a is sent out to an image processor 91b in the control unit 91, and the image processed in the image processor 91b is displayed on the display unit 92. The operator O then operates the manipulator 1 while viewing an image displayed on the display unit 92.

According to such surgical system 90, it is possible to have the advantages of the slack correction mechanism 1 and display unerring images asked for by the operator, and for the operator to put the manipulator into more unerring operation.

As described above, the slack correction mechanism 1 according to the embodiment described herein includes a distal-end pulley 2 that is rotatable with respect to a given axis 2a, a distal-end wire 3 wound around the distal-end pulley 2, a first supporting part 4 including a first base 41, a first friction portion 42 which extends out from the first base 41 and around which the distal-end wire 3 wound around the distal-end pulley 2 is looped on one side and a first coil spring 43 that biases the distal-end wire 3 in a pulling direction on one end side with respect to the first friction portion 42, the first supporting part 4 being adapted to support one side of the distal-end wire 3, and a second supporting part 5 including a second base 51, a second friction portion 52 which extends out from the second base 51 and around which the distal-end wire 3 wound around the distal-end pulley 2 is looped on the other side and a second coil spring 53 that biases the distal-end wire 3 in a pulling direction on the other side with respect to the second friction portion 52, the second supporting part 5 being adapted to support the other side of the distal-end wire 3. It is thus possible to reduce the operational delay of the distal-end member 21 for unerring operation. Further, because the distal-end wire 3 is not looped in its entirety, an assembling steps count diminishes, resulting in improved assembling capability and ease of initial tension adjustment as well. Furthermore, there is no need for using a caulking member or the like for connection of the distal-end wire 3, possibly ending up with smooth operation.

The slack correction mechanism 1 according to the embodiment described herein further includes an interlocking part 6 activated such that when one of the first 4 and the second supporting part 5 moves in a pulling direction of the distal-end wire 3, the other moves in a delivery direction of the distal-end wire 3. It is thus possible to interlock mutual movements of the first 4 and the second supporting part 5 for unerring operation.

The slack correction mechanism 1 according to the embodiment described herein further includes a driving unit 7 for driving the interlocking part 6, and an operating unit 8 that is put by the operator in operation to drive the driving unit 7. It is thus possible to achieve smooth and unerring operation.

In the slack correction mechanism 1 according to the embodiment described herein, the interlocking part 6 includes a pinion 61 that has mating teeth 61a on its outer circumference and rotates with respect to a given axis, and the first supporting part 4 includes a first rack 44 in mesh with the pinion 61 while the second supporting part 5 includes a second rack 54 in mesh with the pinion 61. It is thus possible to achieve unerring operation with the use of a simplified structure.

In the slack correction mechanism 1 according to the embodiment described herein, the interlocking part 6 includes an interlocking pulley 62 having a movable axis, and an interlocking wire 63 wound around the interlocking pulley 62 and fixed at one end to the first base 41 and at the other end to the second base 51. It is thus possible to move the interlocking pulley 62 by means of the interlocking pulley guide 64 for initial tension setting for the distal-end wire 3 and interlocking wire 63, resulting in unerring initial tension adjustment.

In the slack correction mechanism 1 according the embodiment described herein, one end of the distal-end wire 3 is fixed to one end of the first coil spring 43, the other end of the first coil spring 43 is fixed to the first base 41, the other end of the distal-end wire 3 is fixed to one end of the second coil spring 53, and the other end of the second coil spring 53 is fixed to the second base 51. It is thus possible to achieve unerring operation with the use of a simplified structure.

In the slack correction mechanism 1 according to the embodiment described herein, the first supporting part 4 supports one end of the first coil spring 43 and includes a first tension pulley 45 that is movable in a pulling direction of the distal-end wire 3, the other end of the first coil spring 43 is fixed to the first base 41, the second supporting part 5 supports one end of the second coil spring 53 and includes a second tension pulley 55 that is movable in a pulling direction of the distal-end wire 3, the other end of the second coil spring 53 is fixed to the second base 51, the distal-end wire 3 is wound around the first tension pulley 45 on one end side with respect to the first friction portion 43 and fixed at one end to the first base 41, and the distal-end wire 3 is wound around the second tension pulley 55 on the other end side with respect to the second friction portion 53 and fixed at the other end to the second base 51. It is thus possible to make the extension/contraction distance of the first 43 and the second coil spring 53 shorter than achieved in the first embodiment.

The manipulator 10 according to the embodiment described herein includes a distal-end part 11 that takes rotatable hold of the distal-end pulley 21 by pulling or letting out the distal-end wire 3, and a slack correction mechanism 1. In addition to the advantage of the slack correction mechanism 1, it is thus possible for the operator to put the manipulator into unerring operation.

The manipulator system 90 according to one embodiment includes a manipulator 10, a system control unit 91 for controlling the manipulator 10, and a display unit 92 for displaying an image acquired through the manipulator 10, wherein the manipulator 10 includes an endoscope 15a having a viewing optical system, an imaging device and a lighting optical system, and the system control unit 91 displays an image acquired through the endoscope 15a on the display unit 92. In addition to the advantage of the slack correction mechanism 1, it is possible to display unerring images asked for by the operator, and it is possible for the operator to put the manipulator into more unerring operation.

While the embodiments have been each explained with reference to one distal-end wire 3, it is to be understood that a pair of distal-end wires may be each fixedly wound around the distal-end pulley 2, and the distal-end wire 3 may be formed of a single wire, a stranded wire, a knitted wire, a sheet-form wire, and so on.

It is here to be appreciated that the invention is in no sense limited to such embodiments as described above. While the explanation of some embodiments embraces numerous specific details for illustration, it would be obvious to those skilled in the art that diverse variations or modifications made thereto are included within the scope of the invention. In other words, illustrative embodiments of the invention are described without excluding generality from the claimed inventions and imposing any limitation thereon.

REFERENCE SIGNS LIST

1: Slack correction mechanism
2: Distal-end pulley
21: Distal-end member
3: Distal-end wire
4: First supporting part
41: First base
42: First friction portion
43: First biasing portion
44: First rack
45: First tension pulley
46: First tension pulley guide
47: First wall
5: Second supporting part
51: Second base
52: Second friction portion
53: Second biasing portion
54: Second rack
55: Second tension pulley
56: Second tension pulley guide
57: Second wall
6: Interlocking part
61: Pinion
62: Interlocking pulley
63: Interlocking wire
64: Interlocking pulley guide
7: Interlocking pulley guide
8: Surplus absorber
10: Manipulator
11: Distal-end part
13: Tubular portion
90: Surgical system
91: Control unit
92: Display unit

The invention claimed is:

1. A slack correction mechanism comprising:
a distal-end pulley that is rotatable with respect to a given axis;
a distal-end wire wound around the distal-end pulley;
a first supporting part including:
a first base,
a first friction portion which extends out from the first base and around which one end of the distal-end wire is looped, and
a first biasing portion that biases the distal-end wire in a pulling direction on the one end of the distal-end wire with respect to the first friction portion, the first supporting part being adapted to support the one end of the distal-end wire;
a second supporting part including:
a second base,
a second friction portion which extends out from the second base and around which the an other end of the distal-end wire is looped, and
a second biasing portion that biases the distal-end wire in a pulling direction on the other end of the distal-end wire with respect to the second friction portion, the second supporting part being adapted to support the other end of the distal-end wire;
an interlocking part activated such that when one of the first supporting part and the second supporting part moves in a pulling direction of the distal-end wire, the other moves in a delivery direction of the distal-end wire;
an actuator for driving the interlocking part; and
an operating unit that is operated by an operator to drive the actuator;
wherein the interlocking part includes:
an interlocking pulley having a movable axis, and
an interlocking wire wound around the interlocking pulley, one end of the interlocking wire being fixed to the first base and an other end of the interlocking wire being fixed to the second base.

2. The slack correction mechanism according to claim 1, wherein
the one end of the distal-end wire is fixed to one end of the first biasing portion,
one end of the first biasing portion is fixed to the first base,
the other end of the distal-end wire is fixed to one end of the second biasing portion, and
an other end of the second biasing portion is fixed to the second base.

3. A slack correction mechanism according to claim 1, wherein
the first supporting part supports one end of the first biasing portion and includes a first tension pulley that is movable in the pulling direction of the distal-end wire,
an other end of the first biasing portion is fixed to the first base,
the second supporting part supports one end of the second biasing portion and includes a second tension pulley that is movable in the pulling direction of the distal-end wire,
an other end of the second biasing portion is fixed to the second base,
the distal-end wire is wound around the first tension pulley on the one end of the distal-end wire with respect to the first friction portion and fixed at the one end to the first base, and
the distal-end wire is wound around the second tension pulley on the other end of the distal-end wire with respect to the second friction portion and fixed at the other end to the second base.

4. A manipulator comprising:
a distal-end part that takes rotatable hold of the distal-end pulley by pulling or letting out the distal-end wire, and
the slack correction mechanism according to claim 1.

5. A manipulator system comprising:
the manipulator according to claim 4,
a controller comprising hardware, the controller being configured to control the manipulator, and
a display for displaying an image acquired through the manipulator,
wherein the manipulator includes an endoscope having a viewing optical system, an imaging device and a lighting optical system, and
the controller permits an image acquired through the endoscope to be displayed on the display.

6. A slack correction mechanism comprising:
a distal-end pulley that is rotatable with respect to a given axis;
a distal-end wire wound around the distal-end pulley;
a first supporting part including:
  a first base,
  a first friction portion which extends out from the first base and around which one end of the distal-end wire is looped, and
  a first biasing portion that biases the distal-end wire in a pulling direction on the one end of the distal-end wire with respect to the first friction portion, the first supporting part being adapted to support the one end of the distal-end wire;
a second supporting part including:
  a second base,
  a second friction portion which extends out from the second base and around which the an other end of the distal-end wire is looped, and
  a second biasing portion that biases the distal-end wire in a pulling direction on the other end of the distal-end wire with respect to the second friction portion, the second supporting part being adapted to support the other end of the distal-end wire;
an interlocking part activated such that when one of the first supporting part and the second supporting part moves in a pulling direction of the distal-end wire, the other moves in a delivery direction of the distal-end wire;
an actuator for driving the interlocking part; and
an operating unit that is operated by an operator to drive the actuator;
wherein the interlocking part comprises a pinion that has mating teeth on its outer circumference and rotates with respect to a given axis,
the first supporting part includes a first rack in mesh with the pinion,
the second supporting part includes a second rack in mesh with the pinion;
the first supporting part supports one end of the first biasing portion and includes a first tension pulley that is movable in the pulling direction of the distal-end wire,
an other end of the first biasing portion is fixed to the first base,
the second supporting part supports one end of the second biasing portion and includes a second tension pulley that is movable in the pulling direction of the distal-end wire,
an other end of the second biasing portion is fixed to the second base,
the distal-end wire is wound around the first tension pulley on the one end of the distal-end wire with respect to the first friction portion and fixed at the one end to the first base, and
the distal-end wire is wound around the second tension pulley on the other end of the distal-end wire with respect to the second friction portion and fixed at the other end to the second base.

7. A manipulator comprising:
a distal-end part that takes rotatable hold of the distal-end pulley by pulling or letting out the distal-end wire, and
the slack correction mechanism according to claim 6.

8. A manipulator system comprising:
the manipulator according to claim 7,
a controller comprising hardware, the controller being configured to control the manipulator, and
a display for displaying an image acquired through the manipulator,
wherein the manipulator includes an endoscope having a viewing optical system, an imaging device and a lighting optical system, and
the controller permits an image acquired through the endoscope to be displayed on the display.

\* \* \* \* \*